(12) United States Patent
Haldar et al.

(10) Patent No.: US 7,704,528 B2
(45) Date of Patent: Apr. 27, 2010

(54) BINDER COMPOSITION AND METHOD FOR PROCESSING POORLY COMPRESSIBLE DRUGS INTO TABLETS OF PREDETERMINED HARDNESS AND FRIABILITY

(75) Inventors: Rama Haldar, Randolph, NJ (US); John Zamora, Paramus, NJ (US); Dipan B. Ray, Springfield, NJ (US); William Drefko, Kearny, NJ (US); Greg Dubrowny, Garfield, NJ (US); Sidney Etienne, Westbury, NY (US)

(73) Assignee: ISP Investments Inc., Wilmington, DE (US)

( * ) Notice: Subject to any disclaimer, the term of this patent is extended or adjusted under 35 U.S.C. 154(b) by 1713 days.

(21) Appl. No.: 10/641,878

(22) Filed: Aug. 15, 2003

(65) Prior Publication Data

US 2004/0224015 A1   Nov. 11, 2004

Related U.S. Application Data

(60) Provisional application No. 60/486,001, filed on May 5, 2003.

(51) Int. Cl.
*A61K 9/26* (2006.01)
*A61K 9/22* (2006.01)

(52) U.S. Cl. ............ 424/469; 424/464; 424/465; 424/468; 424/489

(58) Field of Classification Search ......... 424/468–490
See application file for complete search history.

(56) References Cited

U.S. PATENT DOCUMENTS

| 5,035,897 | A | * | 7/1991 | Ayer et al. ............ 424/473 |
| 5,037,658 | A | * | 8/1991 | Urban et al. ............ 424/469 |
| 5,684,040 | A | * | 11/1997 | Grabowski et al. ........ 514/457 |
| 5,840,329 | A | * | 11/1998 | Bai ................... 424/458 |
| 2001/0044472 | A1 | * | 11/2001 | Upadhyay et al. ........ 514/629 |

* cited by examiner

*Primary Examiner*—Michael G Hartley
*Assistant Examiner*—Micah-Paul Young
(74) *Attorney, Agent, or Firm*—William J. Davis; Thompson Hine LLP

(57) ABSTRACT

Tablets of a poorly compressible drug are made by direct compression using a binder composition which is a polymer, preferably a copolymer of polyvinylpyrrolidone (PVP) and vinyl acetate (VA), having a defined glass transition temperature (Tg), admixed with a plasticizer, e.g. an organic ester or polyol, which reduces the Tg of the copolymer by at least 10° C. The binder composition and the drug are directly compressed into a tablet of predetermined hardness and friability, and at an acceptable compression force.

17 Claims, No Drawings

BINDER COMPOSITION AND METHOD FOR PROCESSING POORLY COMPRESSIBLE DRUGS INTO TABLETS OF PREDETERMINED HARDNESS AND FRIABILITY

CROSS-REFERENCE TO RELATED PATENT APPLICATION

This application is based upon Provisional Application Ser. No. 60/468,001 filed May 5, 2003.

BACKGROUND OF THE INVENTION

1. Field of the Invention

This invention relates to direct compression of poorly compressible drugs, and, more particularly, to a new and improved binder composition for such drugs, which enables mixtures thereof to be processed into drug tablets of desired hardness and friability by direct compression, and at an acceptable compression force.

2. Description of the Prior Art

Poorly compressible drugs such as naproxen and acetaminophen are currently made into tablets by wet granulation. However, it would be advantageous to provide a method of forming tablets of such drugs by direct compression, which is a more commercially advantageous process.

SUMMARY OF THE INVENTION

Tablets of a poorly compressible drug are made by direct compression using a binder composition which is a mixture of a polymer, e.g. a copolymer of polyvinylpyrrolidone (PVP) and vinyl acetate (VA), hydroxypropyl cellulose, hydroxypropyl methyl cellulose and polyvinylpyrrolidone, having a defined glass transition temperature (Tg), and an effective amount of a plasticizer therewith, to reduce the Tg of said copolymer by at least 10° C. The binder composition and drug are admixed, and formed into a tablet by direct compression at an acceptable compression force. The resultant tablet has an advantageous hardness and friability.

The preferred copolymer is 60 wt. % PVP and 40% VA having a Tg of 106° C., and the plasticizer reduces the Tg of this copolymer by at least 20° C. when present in admixture therewith in an amount of about 1-25 wt. %, preferably 5-15%. Representative plasticizers include polyethylene glycol, triethyl citrate, acetylated fatty acid glycerides, castor oil, dibutyl phthalate, diethyl phthalate, dibutyl sebacate, glycerol, glycerol monostearate, glyceryl triacetate, polyoxyethylene/polyoxypropylene copolymers and propylene glycol. Preferred plasticizers are organic esters and polyols, for example, triethyl citrate and polyethylene glycol.

In general, the binder composition is a free-flowing powder having an average particle size of about 30-90μ.

A typical poorly compressible drug in the invention is naproxen or acetaminophen.

The process of the invention is carried out by direct compression of the admixture of about 1-25 wt. % of the binder composition and at least 50%, preferably 50-90 wt. % of the drug, the rest being other excipients. Direct compression at about 3000-7000 lbs. provides a tablet having a hardness of at least about 8 Kp, generally 8-20 Kp, and a friability of about less than 3%, preferably 1-3%.

DETAILED DESCRIPTION OF THE INVENTION

The invention will now be illustrated in more detail by reference to the following examples.

The test for efficacy of selected polymer and plasticizer is described in the following Example 1, wherein an aqueous dispersion of the components is prepared, mixed well, and dried on a substrate. Then the glass transition temperature Tg is determined and compared to a control (without plasticizer). The criteria for efficacy is a reduction in Tg (with plasticizer) by at least 10° C.

Example 1

Aqueous dispersions of a binder composition of PVP/VA copolymer (60:40 by wt.) and plasticizer were spray dried in a laboratory scale spray dryer. The resultant powders were collected in a plastic bag. The glass transition temperature for each composition was determined and compared to copolymer without plasticizer (control). The results are shown in Table 1 below.

TABLE 1

| Binder Composition | Tg (° C.) |
| --- | --- |
| Copolymer (Control) | 106 |
| Copolymer w/5% PEG* 4000 | 90 |
| Copolymer w/10% PEG* 4000 | 79 |
| Copolymer w/10% TEC** | 82 |

*polyethylene glycol
**triethyl citrate

The data in Table 1 demonstrates that the plasticizer reduced the Tg of the copolymer by at least 10° C., and up to 27° C.

Example 2

Free flowing powders of a binder composition of PVP/VA (60:40) plasticized with added PEG 4000 (5 and 10% w/w) or triethyl citrate (TEC) (5 and 10% w/w), having a particle size of 30μ, and a poorly compressible drug (acetaminophen) were prepared at a wt. ratio of 75:25 drug:binder composition. Then 0.5% silica and 0.5% lubricant were added and the mixture was compressed at a compression force of (lbs) 3000, 5000 or 7000. The hardness and friability values of the resultant tablets are shown in Table 2 below.

TABLE 2

| Binder Composition | Hardness (Kp) @ | | | Friability (%) @ | | |
| --- | --- | --- | --- | --- | --- | --- |
| (Amt, wt. %) | 3000 lb | 5000 lb | 7000 lb | 3000 lb | 5000 lb | 7000 lb |
| Copolymer (Control) | 5.0 | 7.4 | 6.0 | 9.01 | 3.06 | 3.36 |
| Copolymer + PEG (5%) | 13.9 | 17.5 | 22.2 | 0.64 | 0.50 | 0.50 |
| Copolymer + PEG (10%) | 15.3 | 17.1 | 18.7 | 0.34 | 0.28 | 0.27 |
| Copolymer + TEC (5%) | 20.4 | 21.9 | 23.8 | 0.44 | 0.28 | 0.27 |
| Copolymer + TEC (10%) | 19.4 | 24.1 | 26.1 | 0.44 | 0.42 | 0.42 |

The data in Table 2 demonstrates that the drug tablet plasticized with PEG or TEC had a hardness value of 13.9 to 26.1 kP, as compared to only 5 to 7.4 kP for the control. Also friability was reduced from 3-9% for control (copolymer without plasticizer) to only 0.27 to 0.64% with added plasticizer.

Example 3

The properties of the binder compositions of the invention were determined and compared to the copolymer itself as a control. The test powders were prepared in laboratory apparatus (composition A) or in a production minor spray dryer (5'×5') using a rotary wheel atomizer with and without an air broom device (composition B). These copolymers were used as controls, or admixed with plasticizer (composition C) and (composition D). Drying was carried out at an inlet temperature of 150° C., an outlet temperature of 80° C. and a feed temperature of 50° C. The results are given in Table 3 below.

TABLE 3

| | Composition → | | | |
|---|---|---|---|---|
| | | | Binder Composition | |
| Property of Powders | Copolymer | | 89% B + 10% TEC (+1% silica) | 89% B + 10% PEG 4000 (+1% silica) |
| | A (lab) | B (prod. run) | C | D |
| Tg (° C.) | 106.0 | 108.5 | 82.5 | 86.0 |
| Particle size, MV (μ) | 70.0 | 32.8 | 27.5 | 30.3 |
| Flow rate, (g/sec) | 4.12 | 0.95 | 2.32 | 2.23 |

The results in Table 3 show that the binder compositions C and D reduced the Tg of the control copolymers A or B by >20° C., decreased the particle size of the copolymer powders.

Example 4

Typical formulations of binder composition and drug ready for direct compression into tablets are given in Table 4 below.

TABLE 4

| | Formulation | | | |
|---|---|---|---|---|
| | 1 | 2 | 3 | 4 |
| | Amount (parts) | | | |
| Component | | | | |
| Drug (acetaminophen) | 77 | 77 | 77 | 77 |
| Copolymer (60:40 PVP:VA) | | | | |
| 30μ powder | 10 | | | |
| 90μ powder | | 10 | | |
| Binder Composition | — | | | |
| C | | | 10 | |
| D | | | | 10 |
| Other | | | | |
| Auxiliary Binder (MCC 102) | 10 | 10 | 10 | 10 |

TABLE 4-continued

| | Formulation | | | |
|---|---|---|---|---|
| | 1 | 2 | 3 | 4 |
| Disintegrant (Polyplasdone ® XL) | 2 | 2 | 2 | 2 |
| Processing Aid (Silica*) | 1 | 1 | 1 | 1 |

*The presence of amorphous silica as processing aid eases the formation of tablets by direct compression, generally in an amount of 0.1-10% of the composition, preferably 0.1-5%, and most preferably 0.05-3%. Suitable silica is available from Cabosil as M-5P, surface area 200 ± 15 m²/g, and HS-5, surface area 325 ± 25 m²/g.

Example 5

Table 5 below shows the hardness and friability properties of tablets obtained by direct compression of the formulations of Example 4 at various compression forces.

TABLE 5

| | Composition → | | | |
|---|---|---|---|---|
| | Copolymer | | Binder Composition | |
| Property | A | B | C | D |
| Hardness | | | | |
| 3000 K | 3.1 | 7.9 | 10.2 | 7.5 |
| 5000 | 4.1 | 8.4 | 11.7 | 9.2 |
| 7000 | 4.4 | 7.5 | 8.9 | 9.4 |
| Friability | | | | |
| 3000 | 18.0 | 2.1 | 2.7 | 2.5 |
| 5000 | 11.6 | 2.1 | 1.7 | 2.0 |
| 7000 | 10.5 | 2.2 | 1.4 | 2.2 |

The results in Table 5 show that the binder compositions of the invention provide hard tablets with low friability, even with a high amount of drug (77%) present in the tablet.

Example 6

Tablets can be prepared as above using hydroxypropyl cellulose, hydroxypropyl methyl cellulose and polyvinylpyrrolidone as the polymer component in the binder composition. Similar results are obtained.

Example 7

Tablets can be prepared as above using the following as plasticizers: polyethylene glycol, triethyl citrate, acetylated fatty acid glycerides, castor oil, dibutyl phthalate, diethyl phthalate, dibutyl sebacate, glycerol, glycerol monostearate, glyceryl triacetate, polyoxyethylene/polyoxypropylene copolymers and propylene glycol. Similar results are obtained.

While the invention has been described with particular reference to certain embodiments thereof, it will be understood that changes and modifications may be made which are within the skill of the art. Accordingly, it is intended to be bound only by the following claims, in which:

What is claimed is:

1. A process for making tablets of a poorly compressible drug by direct compression, which comprises providing a binder composition which is made by spray drying an aqueous dispersion of a copolymer of polyvinylpyrrolidone (PVR) and vinyl acetate (VA), having a defined glass transition temperature (Tg), and an effective amount of 5-15 wt. % of a plasticizer which is an organic ester or polyol therewith to reduce the Tg of said copolymer by at least 20° C., admixing said binder composition and 50-90 wt. % of said drug, and forming a tablet thereof by direct compression having a predetermined hardness and friability, and at an acceptable compression force.

2. A process according to claim 1 wherein said drug is naproxen or acetaminophen.

3. A process according to claim 1 wherein said copolymer comprises 60 wt. % PVP and 40% VA, having a Tg of about 106° C.

4. A process according to claim 1 wherein the binder composition is a free-flowing powder having an average particle size of about 30-90μ.

5. A process according to claim 1 wherein said plasticizer is triethyl citrate.

6. A process according to claim 1 wherein direct compression is carried out at 3000-7000 lbs. and the tablet has a hardness of at least about 8 kP and a friability of less than about 3.

7. A process according to claim 6 wherein said tablet hardness is about 8-30 kP, and said friability is about 1-3.

8. A binder composition for direct compression of a poorly compressible drug, comprising a free-flowing powder which is a spray dried aqueous dispersion of a copolymer of polyvinylpyrrolidone (PVP) and vinyl acetate (VA), and an effective amount of 5-15 wt. % of a plasticizer which is an organic ester or polyol to reduce the Tg of the polymer by at least 20° C.

9. A binder composition according to claim 8 wherein said copolymer comprises 60 wt. % PVP and 40 wt. % VA, having a Tg of about 106° C.

10. A binder composition according to claim 8 which has an average particle size of about 30-90μ.

11. A binder composition according to claim 8 wherein said plasticizer is triethyl citrate or polyethylene glycol.

12. A binder composition according to claim 8 in which said spray drying is carried out in the presence of silica powder.

13. A mixture of a poorly compressible drug and the binder composition of claim 8.

14. A mixture according to claim 13 which also includes other excipients.

15. A drug tablet formed by the process of claim 1.

16. A drug tablet of claim 15 in which said drug is naproxen or acetaminophen.

17. A drug tablet of claim 15 wherein said drug is present in an amount of about 50-90 wt. % therein.

\* \* \* \* \*